(12) United States Patent
Ferguson

(10) Patent No.: US 10,767,840 B2
(45) Date of Patent: Sep. 8, 2020

(54) FOCUSED LED HEADLAMP WITH IRIS ASSEMBLY

(71) Applicant: RIVERPOINT MEDICAL, LLC, Portland, OR (US)

(72) Inventor: John Thomas Ferguson, Portland, OR (US)

(73) Assignee: RIVERPOINT MEDICAL, LLC, Portland, OR (US)

( * ) Notice: Subject to any disclaimer, the term of this patent is extended or adjusted under 35 U.S.C. 154(b) by 0 days.

(21) Appl. No.: 16/201,818

(22) Filed: Nov. 27, 2018

(65) Prior Publication Data

US 2019/0093862 A1 Mar. 28, 2019

Related U.S. Application Data

(63) Continuation-in-part of application No. 15/583,557, filed on May 1, 2017, now Pat. No. 10,174,912.

(51) Int. Cl.

| F21V 21/084 | (2006.01) |
|---|---|
| F21V 14/08 | (2006.01) |
| F21V 11/10 | (2006.01) |
| F21V 5/00 | (2018.01) |
| A61B 90/35 | (2016.01) |
| F21V 5/04 | (2006.01) |
| A61B 90/30 | (2016.01) |
| A61B 90/50 | (2016.01) |

(Continued)

(52) U.S. Cl.
CPC .............. *F21V 14/08* (2013.01); *A61B 90/30* (2016.02); *A61B 90/35* (2016.02); *A61B 90/50* (2016.02); *F21V 5/008* (2013.01); *F21V 5/04* (2013.01); *F21V 11/10* (2013.01); *F21V 21/084* (2013.01); *A61B 2090/309* (2016.02); *A61B 2090/502* (2016.02); *F21W 2131/20* (2013.01); *F21Y 2115/10* (2016.08)

(58) Field of Classification Search
CPC .... A61B 1/06; G02B 6/06; F21V 5/00; F21V 21/084; F21V 11/10; F21S 4/00; F21S 8/00
See application file for complete search history.

(56) References Cited

U.S. PATENT DOCUMENTS

| 1,705,465 | A | * | 3/1929 | Cameron | ............... F21V 21/145 |
|---|---|---|---|---|---|
| | | | | | 362/105 |
| 3,371,202 | A | * | 2/1968 | Connors | ................... F21V 7/08 |
| | | | | | 362/281 |

(Continued)

OTHER PUBLICATIONS

Cree's New High-Intensity Class of LEDs More than Doubles Performance—LED professional—LED Lighting Technology, Application Magazine CL-DS97 REV 2C, Jun. 1, 2015.

*Primary Examiner* — Ismael Negron
(74) *Attorney, Agent, or Firm* — Timothy E. Siegel Patent Law, PLLC; Timothy E. Siegel

(57) ABSTRACT

A headlamp includes a tubular housing; an electrical conductor entering the housing and connected to an electrical network; an LED assembly with a ceramic substrate and an LED having a light-emitting front surface; an iris assembly with a toroidal housing, an iris diaphragm and an actuator for adjusting the width of the aperture. A prime lens placed in front of the iris diaphragm and having an annular light block provided proximate a rear surface of the prime lens; and an optical assembly with at least a light focusing lens placed in front of the iris assembly.

12 Claims, 5 Drawing Sheets

(51) Int. Cl.
*F21W 131/20* (2006.01)
*F21Y 115/10* (2016.01)

(56) References Cited

U.S. PATENT DOCUMENTS

| | | | |
|---|---|---|---|
| 3,480,836 A | | 11/1969 | Aronstein |
| 4,104,709 A | * | 8/1978 | Kloots .................... F21L 14/00 362/105 |
| 4,596,449 A | * | 6/1986 | Iwata ...................... G02B 7/10 359/696 |
| 4,866,571 A | | 9/1989 | Butt |
| 5,014,159 A | | 5/1991 | Butt |
| 5,769,523 A | * | 6/1998 | Feinbloom ............ F21V 14/085 362/554 |
| 5,774,271 A | * | 6/1998 | Lagerway ............... F21L 14/00 359/649 |
| 5,857,767 A | | 1/1999 | Hochstein |
| 6,712,486 B1 | | 3/2004 | Popovich |
| 7,470,935 B2 | | 12/2008 | Lee |
| 7,572,031 B2 | | 8/2009 | Schultz et al. |
| 7,618,159 B2 | * | 11/2009 | Tamburrino ............ F21V 11/10 362/321 |
| 8,525,214 B2 | | 9/2013 | Lin |
| 9,091,428 B2 | | 7/2015 | Ferguson |
| 9,234,653 B2 | * | 1/2016 | Ferguson ................ F21V 11/10 |
| 9,351,799 B2 | | 5/2016 | Ferguson |
| 9,568,177 B2 | | 2/2017 | Ferguson |
| 9,660,368 B2 | | 5/2017 | Rathbum |
| 10,174,912 B1 | | 1/2019 | Ferguson |
| 2006/0186906 A1 | | 8/2006 | Bottoms et al. |
| 2012/0120635 A1 | * | 5/2012 | Strong .................. F21V 21/084 362/105 |
| 2014/0334132 A1 | | 11/2014 | Ferguson |
| 2014/0334159 A1 | | 11/2014 | Ferguson |
| 2016/0123563 A1 | * | 5/2016 | Ferguson ............. F21V 21/084 362/277 |
| 2016/0207228 A1 | | 7/2016 | Ferguson |

* cited by examiner

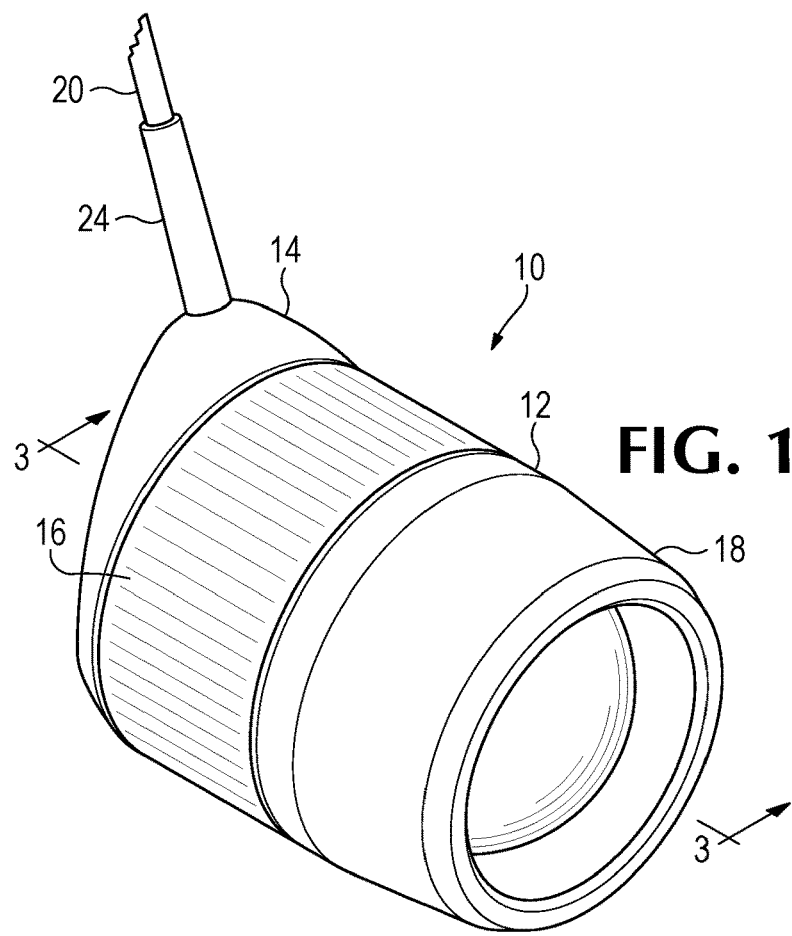
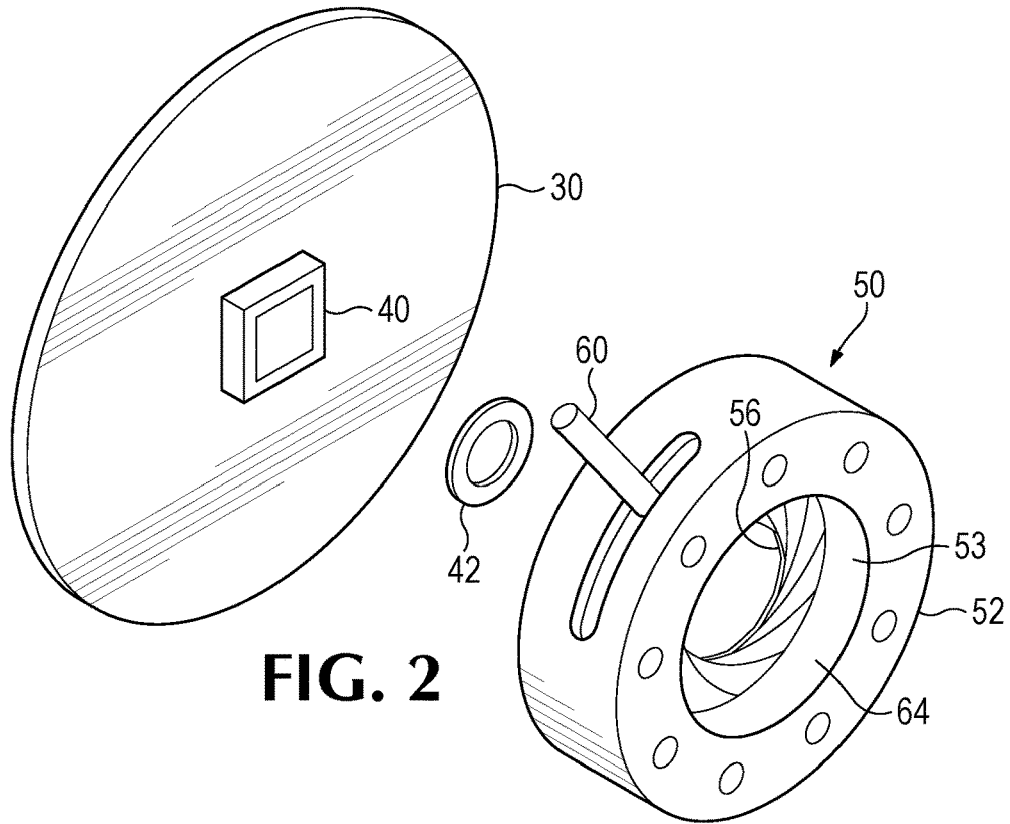

FOCUSED LED HEADLAMP WITH IRIS ASSEMBLY

RELATED APPLICATIONS

This application is a continuation-in-part of U.S. patent application Ser. No. 15/583,557 filed on May 1, 2017 which is incorporated by reference as if fully set for the herein.

BACKGROUND

A medical headlamp is a device for which it is important to produce the maximum amount of light from the minimum amount of electricity. The advent of the light emitting diode (LED), which is a very efficient at turning electricity into light, with a minimum of heat produced, has permitted a great advance in the art. Still, heretofore, LEDs typically were available as part of a package that included a silicone dome lens over the LED. As the light had to pass through the silicone material of the dome lens, some efficiency was lost.

SUMMARY

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other improvements.

In a first separate aspect, the present invention may take the form of a medical headlamp, having a front through which light is emitted. The headlamp has a tubular housing, an electrical conductor, entering the housing, and an electrical network, electrically connected to the electrical conductor. An LED assembly is electrically connected to the electrical network, and this assembly has a front surface, through which light is emitted. Further, a prime lens is placed in front of the LED assembly. An iris assembly is placed in front of the prime lens. This assembly includes a toroidal housing, an iris diaphragm, defining a width-adjustable aperture, seated in the housing and an actuator, permitting a user to adjust the width of the width adjustable aperture. Also, the toroidal housing has an inner surface defining a rear interior space, within the interior surface and to the rear of the iris. A further optical assembly, including at least a light-focusing lens, is placed in front of the iris assembly. Finally, the prime lens has a convex front surface that extends into the rear interior, and an annular light block is placed between the prime lens and the iris diaphragm.

In a second separate aspect, the present invention may take the form of a medical headlamp, having a front through which light is emitted. The headlamp has a tubular housing, an electrical conductor, entering the housing, and an electrical network electrically connected to the electrical conductor. An LED assembly is electrically connected to the electrical network, the LED assembly having a front surface, through which light is emitted. An iris assembly includes a toroidal housing, an iris diaphragm defining a width-adjustable aperture, seated in the housing, and an actuator, permitting a user to adjust the width of the width adjustable aperture. Further, the toroidal housing has a circumferential inner surface defining a front interior space, to the front of the iris diaphragm and a rear interior space, to the rear of the iris diaphragm. The iris assembly is placed so that the iris diaphragm is in front of the LED assembly. Also, a prime lens is placed in front of the iris diaphragm and has a rear surface. A further optical assembly, including at least a light-focusing lens is placed in front of the iris assembly. Finally, the prime lens rear surface has an opaque annular coating, acting as an annular light block.

In addition to the exemplary aspects and embodiments described above, further aspects and embodiments will become apparent by reference to the drawings and by study of the following detailed description.

BRIEF DESCRIPTION OF THE DRAWINGS

Exemplary embodiments are illustrated in referenced drawings. It is intended that the embodiments and figures disclosed herein are to be considered illustrative rather than restrictive.

FIG. 1 is an isometric rendering of a medical headlamp, according to the present invention.

FIG. 2 is an isometric view of some interior elements of the medical headlamp of FIG. 1.

DETAILED DESCRIPTION OF THE PREFERRED EMBODIMENTS

Figure 3:
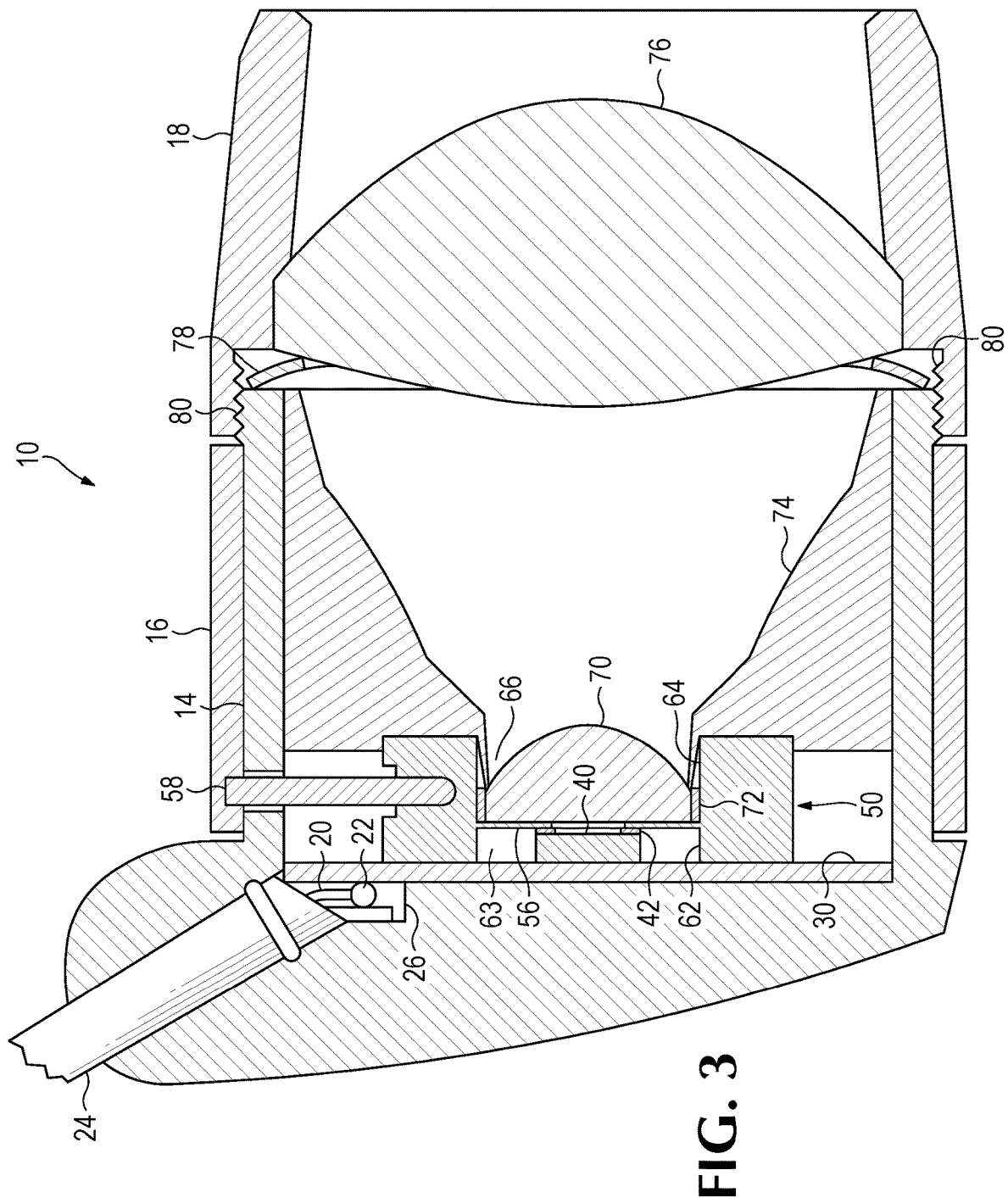
FIG. 3 is a sectional view, taken along line 3-3 of FIG. 1.
Figure 4:
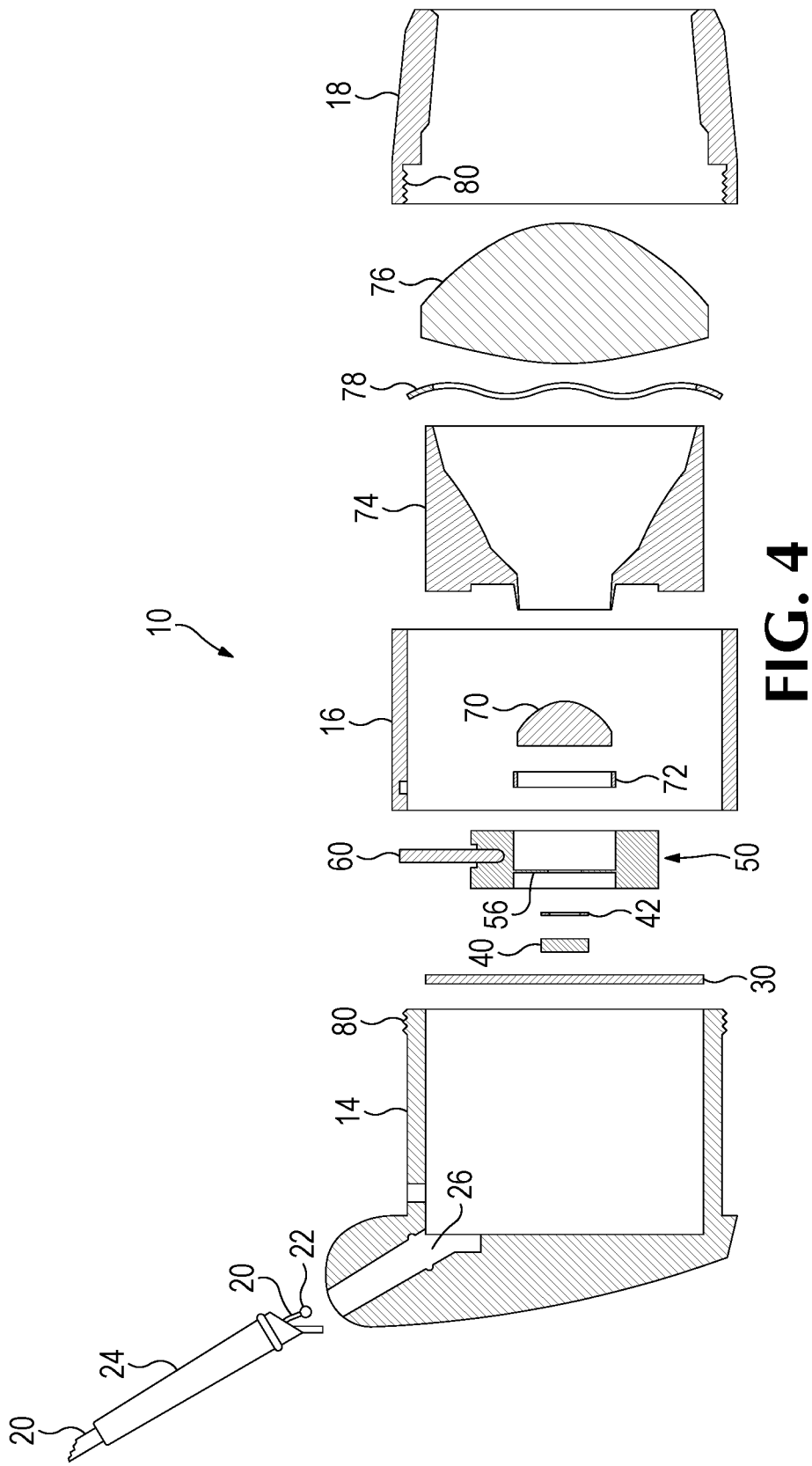
FIG. 4 is an exploded sectional view, taken along line 3-3 of FIG. 1.

Definitions: an LED assembly (or "package") is a light emitting diode (LED) or multiple light emitting diodes mounted closely together, plus immediately physically supporting elements, such as a substrate and electrical terminals. A "chip on board" or "COB" LED assembly is an LED assembly that is made up of multiple LED chips all bonded to a single substrate and typically powered through a single pair of terminals. A "substantially flat LED assembly" has no lens or is capped with a lens that has a radius of curvature of more than 1 mm. Stated slightly differently, a "relatively flat LED assembly" is an LED assembly that is not capped by a lens having a radius of curvature of less than 1 mm. A "bare LED assembly" is one which specifically does not include a light reflecting lens over the LED. Something that is "tubular" or a "tube" could have any closed shape in cross-section, such as a circle, a rectangle or a hexagon, for example.

In a first preferred embodiment, a medical headlamp 10 (also referred to as a bezel) includes a housing 12, made up of an aft barrel 14, a rotating adjustment collar 16 and an exit lens holder 18. A wire 20, terminating in a contact bead 22 (FIG. 3) is held within a boot 24 that extends through an opening 26 (FIG. 3) in the aft barrel 14. A ceramic substrate 30 (FIG. 2) supports an electrical circuit (not shown) that powers an LED assembly 40, which in one embodiment is a COB LED assembly. Ceramic substrate 30 includes an electrical contact pad (not shown) on its rear surface, which during assembly is pushed into contact bead 22, partially crushing it and establishing a robust electrical connection. Details of this process will be described further, below. For ease of presentation only one contact bead 22 has been shown, but an anode and cathode bead 22 are used in a preferred embodiment, separated by a "Y" structure in the boot 24 to keep the two contact beads separated during and after placement, and to prevent wire 20 from being accidentally torn out of housing 12.

A light block 42 is either positioned directly on the surface of LED assembly 40 or held directly in front of it. In varying embodiments, light block 42 is 25 microns (1 mil) to 500 microns (0.02") thick. In front of the light block 42 there is an iris assembly 50 (which may also be termed "an adjustable light block") having a toroidal housing 52, and a set of iris blades 56 (alternatively termed an "iris diaphragm") that retract into and extend out of the housing 52 into the space defined by an inner circumferential surface 53 of the toroidal housing 52, to create a variable sized aperture, according to the position of an actuator 58 (FIG. 3).

The iris blades 56 are not at the rear or the front of the circumferential surface 53 so that a rear margin and a front margin is defined between the iris blades 56 and the rear and the front, respectively, with the rear margin 62 defining a rear interior space 63 and the front margin 64 defining a front interior space 66. The iris assembly 50 is positioned so that LED assembly 40 fits in the rear interior space. In one preferred embodiment, LED assembly 40 includes a lens that extends into the aperture between the iris blades 56. The actuator 58 is in the form of a pin 60 (FIG. 2) and the rotatable collar 16, joined together. The pin 60 extends through a circumferential slot in the aft barrel 14 to connect to collar 16, which is rotated to adjust the size of the iris opening.

A prime lens 70 (which may also be termed a light-focusing lens) is fitted into the front interior space 66, with a heat-shrink PTFE collar 72 to facilitate insertion and smooth any discrepancies in the fit. Forward of lens 70, a lens cone 74 reflects any stray light forward. Finally, an exit lens 76 is held in the exit lens holder 18, against a circular spring 78, which is interposed between exit lens 76 and lens cone 74. Exit lens holder 18 is threaded onto aft barrel 14 at threads 80. In an alternative embodiment, prime lens 70 is interposed between the iris blades. In an additional alternative embodiment, exit lens 76 and prime lens 70 are replaced by a single lens, that combines the functions of both lenses.

Two features of the assembly of headlamp 10, facilitate the efficient manufacture of a robust product. As noted above, the contact bead 22 is held in place by boot 24 and ceramic substrate 30. During assembly, as exit lens holder 18 is threaded onto aft barrel 14 at threads 80, lens cone 74 is pressed against substrate 30, which eventually crushes bead 22, forming a robust contact with the contact pad on the rear of substrate 30.

In addition, in systems using an iris, a time-consuming task of adjusting the maximum size aperture created by the withdrawal of blades 56 into housing 52, is often faced by assembly personnel. At some point, if the blades are withdrawn too far, the aperture they create deviates far from a perfect circle, creating an irregular spot of light, that gives the impression that the device is cheaply made. To avoid this problem, the iris is adjusted during assembly to set a maximum aperture size. But in the use of device 10, the light block 42 sets the appearance of the light spot when the iris blades 56 are withdrawn far enough to be outside the beam created by light block 42. Accordingly, there is no need to set a maximum aperture size, thereby easing the task of assembly.

The headlamp described above can generally produce more light per unit of power applied to it than previously available headlamps. It is also more compact, thereby reducing total headlamp weight. In a preferred embodiment, the headlamp produces between 130-140 lumens per watt and runs between three and four Watts with a weight ranging from two to four ounces. In one preferred embodiment, bare LED assembly 40 is a Cree® XP-L High Intensity LED, chosen from the different options listed in Table 1, below:

TABLE 1

| Chromaticity | | | Minimum Luminous Flux (lm) @ 1050 mA | | Order Codes | |
|---|---|---|---|---|---|---|
| Kit | CCT | Code | Flux (lm) @ 85° C. | Flux (lm) @ 25° C.* | 65 CRI Typical | 70 CRI Minimum |
| 51 | 6200K | V2 | 400 | 446 | XPLAWT-H0-0000V2051 | XPLAWT-H0-000BV2051 |
|  |  | U6 | 380 | 424 | XPLAWT-H0-0000U6051 | XPLAWT-H0-000BU6051 |
|  |  | U5 | 360 | 401 | XPLAWT-H0-0000U5051 | XPLAWT-H0-000BU5051 |
| 53 | 6000K | V2 | 400 | 446 | XPLAWT-H0-0000V2053 | XPLAWT-H0-000BV2053 |
|  |  | U6 | 380 | 424 | XPLAWT-H0-0000U6053 | XPLAWT-H0-000BU6053 |
|  |  | U5 | 360 | 401 | XPLAWT-H0-0000U5053 | XPLAWT-H0-000BU5053 |
| 50 | 6200K | V2 | 400 | 446 | XPLAWT-H0-0000V2050 | XPLAWT-H0-000BV2050 |
|  |  | U6 | 380 | 424 | XPLAWT-H0-0000U6050 | XPLAWT-H0-000BU6050 |
|  |  | U5 | 360 | 401 | XPLAWT-H0-0000U5050 | XPLAWT-H0-000BU5050 |
| E1 | 6500K | V2 | 400 | 446 | XPLAWT-H0-0000V20E1 | XPLAWT-H0-000BV20E1 |
|  |  | U6 | 380 | 424 | XPLAWT-H0-0000U60E1 | XPLAWT-H0-000BU60E1 |
|  |  | U5 | 360 | 401 | XPLAWT-H0-0000U50E1 | XPLAWT-H0-000BU50E1 |
| E2 | 5700K | V2 | 400 | 446 | XPLAWT-H0-0000V20E2 | XPLAWT-H0-000BV20E2 |
|  |  | U6 | 380 | 424 | XPLAWT-H0-0000U60E2 | XPLAWT-H0-000BU60E2 |
|  |  | U5 | 360 | 401 | XPLAWT-H0-0000U50E2 | XPLAWT-H0-000BU50E2 |

In one embodiment, headlamp 10 is connected to a headband assembly, such as that shown and described in U.S. Pat. No. 9,351,799, which is owned by the assignee of this application.

Figure 5:
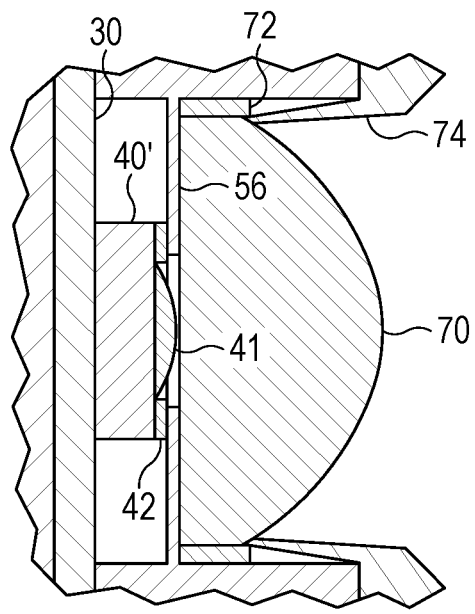
FIG. 5 is a sectional view of a distinguishing detail of an alternative embodiment, taken in plane 3-3 of FIG. 1.
Figure 6:
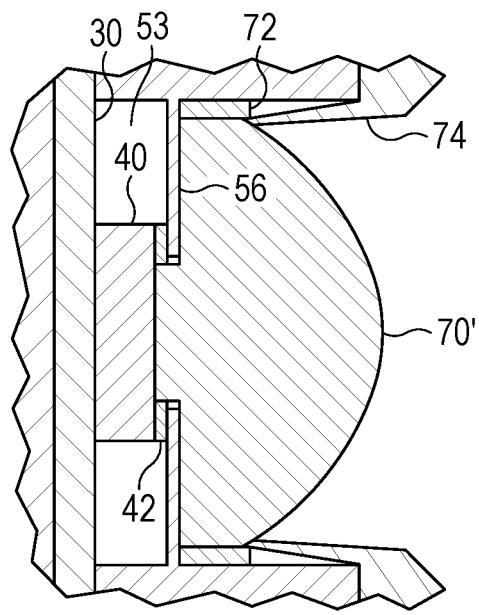
FIG. 6 is a sectional view of a distinguishing detail of an additional alternative embodiment, taken in plane 3-3 of FIG. 1.

Referring now to FIG. 5, in one embodiment, LED assembly 40' includes a shallow lens 41, having radius of curvature of greater than 1 mm and that extends into the aperture defined by iris blades 56. In an additional preferred embodiment, light block 42 is absent. Referring to FIG. 6, in one embodiment, lens 70' extends through the aperture defined by iris blades 56 and light block 42. In alternative embodiments, light block 42 is absent. In another alternative, light block 42 is present, but lens 70' does not extend through the aperture defined by light block 42, or only extends part way through.

Figure 7:
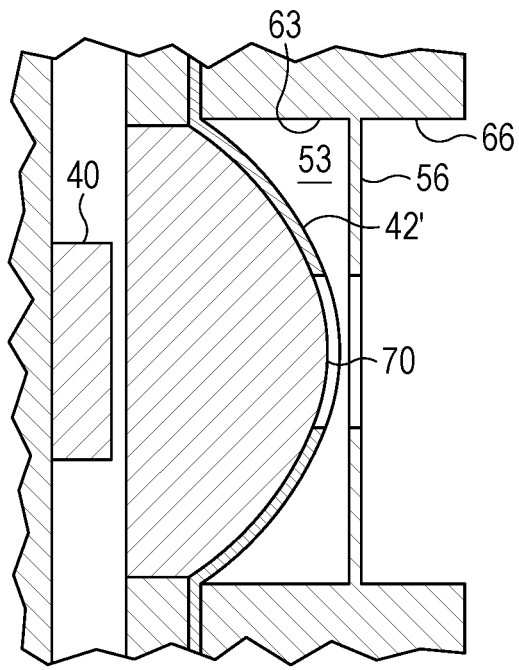
FIG. 7 is a sectional view of a distinguishing detail of yet another additional alternative embodiment, taken in plane 3-3 of FIG. 1.

In a further embodiment, shown in FIG. 7, prime lens 70 extends into rear interior space 63, and an annular light block 42' is interposed between lens 70 and iris blades 56. In some embodiments, light block 42' is conformal to the front surface of lens 70 as shown, but in other embodiments (not shown) it is not conformal, and may be flat, or only partially conformal. When the iris blades 56 are open beyond a particular point, the beam is shaped only by light block 42', providing a nicely round and crisp beam.

Figure 8:
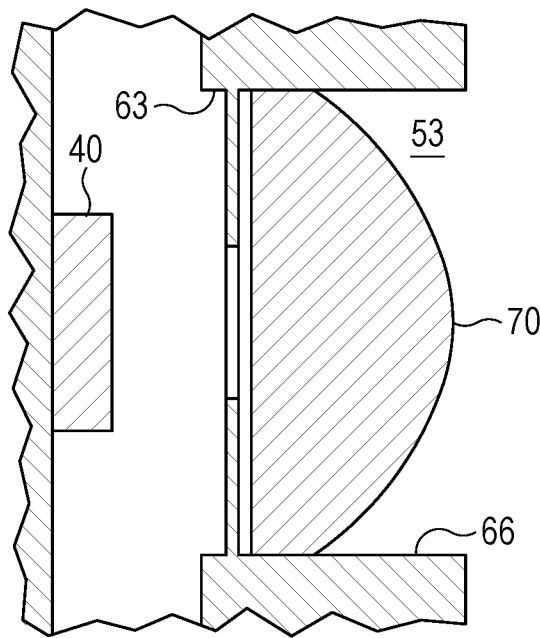
FIG. 8 is a sectional view of a distinguishing detail of still another additional alternative embodiment, taken in plane 3-3 of FIG. 1.
Figure 9:
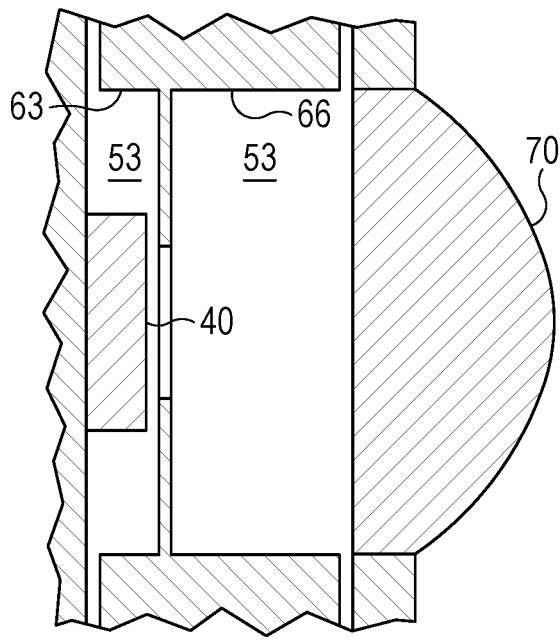
FIG. 9 is a sectional view of a distinguishing detail of still another additional alternative embodiment, taken in plane 3-3 of FIG. 1.
Figure 10:
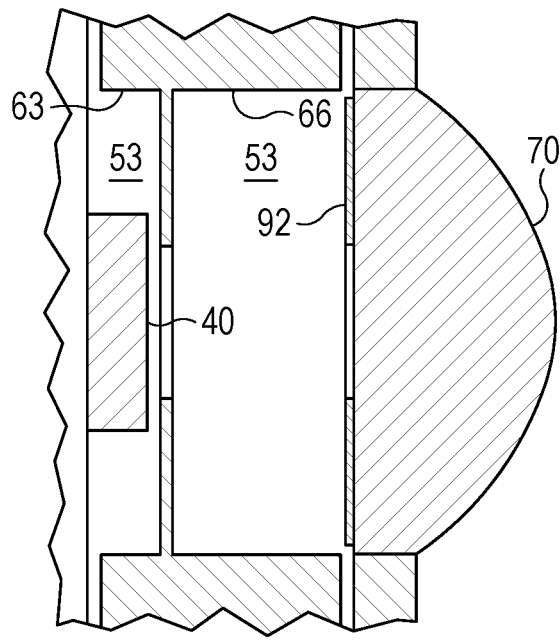
FIG. 10 is a sectional view of a distinguishing detail of still another additional alternative embodiment, taken in plane 3-3 of FIG. 1.

Referring to FIG. 8, prime lens 70 is positioned in front interior space 66. The closeness between the rear of prime lens 70 and iris blades 56 yields beneficial optical qualities. In still another embodiment, illustrated in FIG. 9, the LED assembly 40 extends into the rear interior space 63, and the prime lens 70 is outside of the front interior space 66, with no interposed annular light block. Finally, FIG. 10 shows a detail view of an embodiment similar to that of FIG. 9, but with an opaque, annular coating 92 on the rear of prime lens 70, acting as a light block. Such an embodiment reduces manufacturing costs, as there is no need for a separate light block.

While a number of exemplary aspects and embodiments have been discussed above, those possessed of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

The invention claimed is:

1. A headlamp comprising:
 (a) a tubular housing having a rear and a front;
 (b) an electrical conductor, entering said housing and connected to an electrical network;
 (c) an LED assembly having a light-emitting front surface, connected to the electrical conductor;
 (d) a prime lens placed in front of said LED assembly;
 (e) an iris assembly including a toroidal housing with an inner surface defining an interior space to the rear of the iris assembly, an iris diaphragm seated in the toroidal housing and defining a width adjustable aperture and an actuator for adjusting the width of said width adjustable aperture, said iris assembly provided in front of the prime lens;
 (f) an annular light block placed between said prime lens and said iris diaphragm; and
 (g) an optical assembly including at least one light focusing lens placed in front of said iris assembly,
 wherein said prime lens has a convex front surface that extends into said interior space.

2. The headlamp of claim 1, wherein said light-emitting front surface is flat.

3. The headlamp of claim 1, wherein said annular light block is formed over said front surface of said prime lens.

4. The headlamp of claim 1, further comprising a gap between said LED assembly and said iris diaphragm.

5. The headlamp of claim 1, wherein said prime lens includes a rear surface and wherein said light-emitting front surface abuts said rear surface.

6. The headlamp of claim 1, wherein said prime lens includes a rear surface and wherein a space separates said light-emitting front surface from said rear surface.

7. The headlamp of claim 1, wherein said actuator includes an element that protrudes through said toroidal housing and said tubular housing, said element configured to be actuated by a user.

8. A headlamp comprising:
 (a) a tubular housing having a rear and a front;
 (b) an electrical conductor entering said housing and connected to an electrical network;
 (c) an LED assembly having a light-emitting front surface connected to the electrical conductor;
 (d) an iris assembly including a toroidal housing, with a circumferential inner surface defining a front interior space toward the front of the iris assembly and a rear interior space toward the rear of the iris assembly, an iris diaphragm seated in the toroidal housing and defining a width adjustable aperture, and an actuator for adjusting the width of said width adjustable aperture, said iris assembly being placed so that said iris diaphragm is in front of said LED assembly;
 (e) a prime lens placed in front of said iris diaphragm, and having a rear surface provided with an opaque annular coating forming an annular light block; and
 (f) a further optical assembly, including at least one light focusing lens placed in front of said prime lens.

9. The headlamp of claim 8, wherein said prime lens is placed entirely in front of said iris assembly.

10. The headlamp of claim 8, wherein said prime lens is placed partially in said front interior space.

11. The headlamp of claim 8, wherein said LED assembly protrudes into said rear interior space.

12. The headlamp of claim 8, wherein said actuator includes an element that protrudes through said toroidal housing and said tubular housing, said element configured to be actuated by a user.

\* \* \* \* \*